United States Patent
Wegman et al.

(10) Patent No.: US 10,119,131 B2
(45) Date of Patent: Nov. 6, 2018

(54) COMPOSITIONS AND METHODS FOR PRODUCING CLOSTRIDIAL COLLAGENASES

(75) Inventors: Thomas L. Wegman, N. Merrick, NY (US); Bo Yu, Fresh Meadows, NY (US)

(73) Assignee: BIOSPECIFICS TECHNOLOGIES CORP., Lynbrook, NY (US)

(*) Notice: Subject to any disclaimer, the term of this patent is extended or adjusted under 35 U.S.C. 154(b) by 177 days.

(21) Appl. No.: 13/422,939

(22) Filed: Mar. 16, 2012

(65) Prior Publication Data

US 2012/0237497 A1 Sep. 20, 2012

Related U.S. Application Data

(60) Provisional application No. 61/453,285, filed on Mar. 16, 2011.

(51) Int. Cl.
*C12N 9/52* (2006.01)
*C12N 1/20* (2006.01)
*A61K 38/48* (2006.01)
*C12P 21/06* (2006.01)

(52) U.S. Cl.
CPC ............ *C12N 9/52* (2013.01); *A61K 38/4886* (2013.01); *C12N 1/20* (2013.01); *C12Y 304/24003* (2013.01); *C12P 21/06* (2013.01)

(58) Field of Classification Search
None
See application file for complete search history.

(56) References Cited

U.S. PATENT DOCUMENTS

| | | | | |
|---|---|---|---|---|
| 3,821,364 A | * | 6/1974 | Chiulli | 424/94.67 |
| 4,524,065 A | | 6/1985 | Pinnell | |
| 5,252,481 A | * | 10/1993 | Holjevac et al. | 435/252.7 |
| 5,830,741 A | | 11/1998 | Dwulet et al. | |
| 6,086,872 A | | 7/2000 | Wegman | |
| 2007/0224183 A1 | * | 9/2007 | Sabatino et al. | 424/94.63 |
| 2010/0086971 A1 | * | 4/2010 | Suppmann | C12N 1/20 435/71.2 |

FOREIGN PATENT DOCUMENTS

| | | |
|---|---|---|
| EP | 0468411 A2 | 1/1992 |
| EP | 2130551 * | 12/2009 |
| EP | 2133415 A1 | 12/2009 |
| RU | 2180002 C2 | 7/2001 |
| WO | WO 2007/089851 A2 | 8/2007 |

OTHER PUBLICATIONS

Bonnerjea J et al. (1986). Protein purification: the right step at the right time. Biotechnology, v4, p. 954-958.*
Kågedal L et al. (1991). Chemical, physical, and chromatographic properties of Superdex 75 prep grade and Superdex 200 prep grade gel filtration media. Journal of Chromatography A, v537, p. 17-32.*
Office Action issued in Canadian Application No. 2,643,171, 3 pages (dated Mar. 1, 2012).
International Search Report and Written Opinion in corresponding Application No. PCT/US2012/029492, 19 pages. (dated Aug. 20, 2012).

* cited by examiner

*Primary Examiner* — Sean C. Barron
(74) *Attorney, Agent, or Firm* — Rothwell, Figg, Ernst & Manbeck, p.c.

(57) ABSTRACT

The present invention provides a method for producing a drug product comprising a combination of highly purified collagenase I and collagenase II from *Clostridium histolyticum*. The method utilizes an improved medium for the cultivation of *Clostridium histolyticum* which includes a non-meat-derived (i.e., non-mammalian) peptone or vegetable peptone. The method includes one or more of: (1) reducing glucose content in the meat-free or vegetable-derived media; and (2) increasing the salt concentration in the meat-free or vegetable-derived media. Also provided is a drug product which includes collagenase I and collagenase II at an optimized fixed mass ratio, and which has a purity of greater than at least 95%.

19 Claims, 3 Drawing Sheets

COMPOSITIONS AND METHODS FOR PRODUCING CLOSTRIDIAL COLLAGENASES

RELATED APPLICATIONS

This application claims the benefit of U.S. Provisional Application No. 61/453,285, filed Mar. 16, 2011, the entire disclosure of which is fully incorporated herein.

BACKGROUND OF THE INVENTION

Collagen is the major structural constituent of mammalian organisms and makes up a large portion of the total protein content of skin and other parts of the animal body. In humans, it is particularly important in the wound healing process and in the process of natural aging. Various skin traumas such as burns, surgery, infection and accident are often characterized by the erratic accumulation of fibrous tissue rich in collagen and having increased proteoglycan content. In addition to the replacement of the normal tissue which has been damaged or destroyed, excessive and disfiguring deposits of new tissue sometimes form during the healing process. The excess collagen deposition has been attributed to a disturbance in the balance between collagen synthesis and collagen degradation.

Numerous diseases and conditions are associated with excess collagen deposition and the erratic accumulation of fibrous tissue rich in collagen. Such diseases and conditions are collectively referred to herein as "collagen-mediated diseases". Collagenase, an enzyme that has the specific ability to digest collagen, has been used to treat a variety of collagen-mediated diseases. Collagenase formulations have a broad variety of uses in the medical field, including their use as therapeutics.

Collagenase for use in therapy may be obtained from a variety of sources including mammalian (e.g. human), crustacean (e.g. crab, shrimp), fungal, and bacterial (e.g., from the fermentation of *Clostridium, Streptomyces, Pseudomonas*, or *Vibrio*). Collagenase has also been genetically engineered. One common source of crude collagenase is from a bacterial fermentation process, specifically the fermentation of *Clostridium histolyticum* ("*C. histolyticum*"). The crude collagenase obtained from *C. histolyticum* may be purified using any of a number of chromatographic techniques.

Collagenases from *C. histolyticum*, i.e., collagenase class I and class II, are of particular importance, e.g., for dissociation of organ tissue in vitro. Importantly, collagenase digestion of pancreatic tissue is presently used in the preparation and isolation of human islet cells. However, a number of other different specific cell types have been isolated from attendant connective tissue, including fat cells from adipose tissue, hepatocytes from liver, chondrocytes from cartilage, myocytes from heart, and osteoblasts from bone. (Ian Freshney, Culture of animal cells, A Manual of Basic Technique, Alan R Liss Inc., 1987.)

A practical advantage of using *C. histolyticum* for the production of collagenases is that it can be cultured in large quantities in simple liquid media, and it regularly produces amounts of proteolytic enzymes which are secreted into the culture medium.

As used herein, "meat" culture refers to a culture of cells grown in the presence of tissue derived from a mammal. "Meat" is not intended to include poultry or fish. As used herein, "meat-derived" and "animal-derived" are used interchangeably. Particularly, bovine products have been used in culture media in the fermentation of *C. histolyticum*, but they run the risk of contamination by agents which cause transmissible spongiform encephalopathies (TSEs; e.g., prions associated with bovine spongiform encephalopathy or "mad cow disease"). A known meat culture is the H4 strain of *Clostridium histolyticum*, which was developed in Dr. I. Mandl's laboratory at Columbia University in 1956. A further meat culture has been derived from the H4 strain named the ABC *Clostridium histolyticum* master cell bank, which has been deposited as ATCC 21000.

U.S. Pat. No. 7,811,560 ("the Auxilium '560 patent"), which is incorporated herein by reference in its entirety, discloses methods of producing collagenases without using meat-derived media. Using soybean derived fermentation medium, the methods described therein generated separately highly purified collagenase I and II, which were recombined in a 1:1 ratio to produce a drug product. The Auxilium '560 patent also discloses methods of producing highly purified collagenases using culture media containing porcine-derived products.

U.S. Patent Publication 2010/0086971 ("the Roche patent publication"), which is also incorporated herein by reference in its entirety, discloses numerous fermentation recipes which are based on vegetable peptone, including soybean-derived peptone, or vegetable-derived peptone plus fish gelatin. The Roche patent publication discloses successful growth of *Clostridium* and collagenase/gelatinase activities in these medium conditions, and does not disclose measuring clostripain. However, in another Roche patent U.S. Pat. No. 7,956,167, the inventors disclose that clostripain activity in the clostridia fermentation broth for downstream purification is "even more preferred between about 100 and 200 U per mg total collagenase".

One drawback to known methods of fermenting *Clostridium* for the purposes of isolating collagenase is the production of contaminating proteases such as clostripain. Clostripain, a cysteine protease, is believed to be a major cause of collagenase degradation and instability. When proteases are present in a crude collagenase mixture, researchers must take extra precautions to neutralize the proteases, including making use of protease inhibitors, such as leupeptin, and performing all of the purification steps in specially designed cold rooms with chilled solutions. Theoretically, there are two approaches to dealing with the clostripain problem: one approach focuses on the downstream process, i.e., developing a purification method to remove clostripain as early as possible; the second approach is to develop a method to reduce clostripain production during the fermentation stage.

Thus, the art is in need of improved methods of culturing *C. histolyticum*. In view of this it is an objective of the invention to provide alternative methods and compositions for vegetable-derived media to support the growth of *C. histolyticum* and produce collagenase I and II in amounts which can be highly purified from culture supernatant in the absence of other contaminating proteases such as clostripain.

The inventors have surprisingly found that various components found in prior art fermentation media have a significant impact on the generation of clostripain, which leads to degradation of the desired collagenase I and II later in the purification process. Specifically, the inventors have found that either (1) minimizing the glucose content in the meat-free or vegetable-derived media; or (2) increasing the salt concentration in the meat-free or vegetable-derived media; or a combination of the two approaches, fulfills the above objective.

SUMMARY OF THE INVENTION

The present invention provides a method for producing a collagenase composition comprising a combination of highly purified collagenase I and collagenase II obtained by fermenting *C. histolyticum* in medium free of animal material-derived ingredients. In particular, the composition or drug product obtained by the method is substantially clostripain-free, and thus highly stable. By "substantially free" is meant less than 10 U per mg total collagenase as determined by the assay in example 8 and more preferably less than 5 U/mg, and most preferably about 1 U/mg or less; and/or (3) no visible band representing clostripain and/or degraded collagenase on SDS-PAGE gel compared to a reference standard.

The present invention also provides fermentation media for *Clostridium histolyticum*, wherein the components of the medium have been optimized such that collagenase I and II are efficiently produced and the production of clostripain is inhibited.

The inventors have found that glucose in a meat-free or vegetable-derived medium can support the production of clostripain in the medium, which can, in turn, cause the degradation of the desired collagenases. Thus, in one aspect, the invention provides a "low glucose" meat-free or vegetable-derived medium for the fermentation of *C. histolyticum*. A "low glucose" meat-free or vegetable-derived medium preferably contains less than about 5 g/L glucose, more preferably less than about 1 g/L, even more preferably less than about 0.5 g/L glucose, or can even be glucose-free.

The inventors have also found that using high salt concentrations in the growth media can reduce the amount of clostripain produced in culture. Thus, in another aspect, the invention provides a "high salt" meat-free or vegetable-derived medium for the fermentation of *C. histolyticum*. By "high salt" is meant greater than about 5 g/L (or 0.5% w/v) total salt, more preferably greater than about 7.5 g/L (or 7.5%) total salt, and more preferably about 9 g/L (or 9%) or more. It is contemplated that any salt known to be suitable for use in microbiological fermentation media may be used in the current invention. In a preferred embodiment, chloride, phosphate or sulfate salts may be used. In a more preferred embodiment, the salts may be sodium chloride, potassium chloride, monosodium phosphate, disodium phosphate, tribasic sodium phosphate, potassium monophosphate, potassium diphosphate, tripotassium phosphate, calcium chloride, magnesium sulfate or various combinations thereof. In certain embodiments, potassium diphosphate may be about 0.1-0.3%, potassium phosphate may be about 0.75% to 0.175%, sodium phosphate may be about 0.2-0.5%, and/or sodium chloride may be about 0.15-0.35%. Preferably, the medium further comprises magnesium sulfate and vitamins, including, riboflavin, niacin, calcium pantothenate, pimelic acid, pyridoxine and thiamine.

In yet another aspect, the invention provides a collagenase composition or product obtained through the process of the invention which may contain a mass ratio of collagenase I and collagenase II which is modified or optimized to produce a desired or even a maximal synergistic effect. In certain embodiments, the collagenase I to collagenase II mass ratio is about 0.5 to 1.5, more preferably 0.6 to 1.3, even more preferably 0.8 to 1.2, and most preferably, 1 to 1.

In still other aspects, the invention provides pharmaceutical formulations and methods for treating patients suffering from a collagen-mediated disease using a collagenase composition of the invention.

Yet a further aspect of the invention is a method for cultivating *Clostridium histolyticum* in a meat-free or vegetable-derived medium, wherein the medium is "low glucose" or "high salt" or both.

The currently claimed methods result in the surprising reduction in the amount of clostripain produced in cultures of *Clostridium histolyticum*, thus eliminating the need for adding protease inhibitors such as leupeptin to reagents and allowing researchers to conduct all purification steps at ambient temperature. The foregoing and other objects, features and advantages of the invention will be apparent from the following more particular description of preferred embodiments of the invention.

BRIEF DESCRIPTION OF THE DRAWINGS

Lane 1: Marker
Lane 2: Marker
Lane 3: M #1 seed culture
Lane 4: M #3
Lane 5: M #3+additional yeast extract
Lane 6: M #3−salt
Lane 7: M #3+glucose
Lane 8: M #3−salt/+glucose
Lane 9: M #3
Lane 10: M #3+additional yeast extract
Lane 11: M #3−salt
Lane 12: M #3+glucose
Lane 13: M #3−salt/+glucose
Lane 14: Marker

Lane 1: Marker
Lane 2: M #1
Lane 3: M#3 (phytone)
Lane 4: M #4 (VEGGIETONE (vegetable peptone))
Lane 5: M #3+glucose
Lane 6: M #4+glucose
Lane 7: M #3 (phytone)
Lane 8: M #4+glucose
Lane 9: M #3+glucose
Lane 10: M #4+glucose
Lane 11 Marker
Lane 12: Marker

Lane 1: Marker
Lane 2: seed culture
Lane 3: 5% OXOID VG 0100/1 mM $CaCl_2$
Lane 4: M #4
Lane 5: M #4−salt+1 mM $CaCl_2$ Lane 6: M #3
Lane 7: M #4
Lane 8: M #4-salt+1 mM CaCl$_2$
Lane 9: M #3
Lane 10: Marker
Lane 11: Marker

DETAILED DESCRIPTION OF THE INVENTION

The invention provides a method for producing collagenases by fermenting *C. histolyticum* in a meat-free or vegetable-derived medium, wherein the culture supernatant is substantially clostripain-free. The collagenases so produced can be isolated, purified, and combined to provide a composition comprising a mixture of collagenase I and collagenase II in an optimized fixed mass ratio which is substantially clostripain-free. It is understood that the terms "drug substance", "drug product" or "collagenase composition" can be used interchangeably.

In one embodiment of the invention, a fermentation process is described. The crude collagenase obtained from fermentation of *C. histolyticum* may be purified by a variety of methods known to those skilled in the art, including dye ligand affinity chromatography, heparin affinity chromatography, ammonium sulfate precipitation, hydroxylapatite chromatography, size exclusion chromatography, ion exchange chromatography, and/or metal chelation chromatography. Additionally, purification methods for collagenases are known, such as, for example, those described in the Auxilium '560 patent.

Both collagenase I and collagenase II are metalloproteases and require tightly bound zinc and loosely bound calcium for their activity (Eddie L. Angleton and H. E. Van Wart, *Biochemistry* 1988, 27, 7406-7412). Both collagenases have broad specificity toward all types of collagen (Steinbrink, D; Bond, M and Van Wart, H; (1985), *JBC*, 260 p 2771-2776). Collagenase I and Collagenase II digest collagen by hydrolyzing the triple-helical region of collagen under physiological conditions (Steinbrink, D; Bond, M and Van Wart, H; (1985), *JBC*, 260 p 2771-2776). Even though each collagenase shows different specificity (e.g. each have a different preferred target amino sequence for cleavage), together, they have synergistic activity toward collagen [Mandl, I., (1964), *Biochemistry*, 3: p. 1737-1741; Vos-Scheperkeuter, G H, (1997), *Cell Transplantation*, 6: p. 403-412]. Collagenase II has a higher activity towards all kinds of synthetic peptide substrates than collagenase I as reported for class II and class I collagenase in the literatures. [Bond, M. D. (1984), *Biochemistry*, 23: p. 3085-3091. Hesse, F, (1995), *Transplantation Proceedings*, 27: p. 3287-3289].

A "peptone" is understood as being a mixture of any of various water-soluble compounds that form as intermediates during hydrolysis of proteins to amino acids. A peptone is frequently obtained by enzymatic digestion or acid hydrolysis of natural products, such as animal tissues, milk, plants or microbial cultures. In nutrient media for growing microorganisms such as bacteria and fungi, peptones and gelatins can serve as an organic source, e.g., for carbon and/or nitrogen.

Frequently, the protein source for the production of a peptone is a waste form arising during the production of meat and dairy produce. However, a variety of peptones are available from plant sources. Depending on the source material and any processing thereof (such as purification to a certain degree of the proteinaceous components of the source) before hydrolytic treatment, a number of compounds other than peptides or amino acids can be part of a peptone.

The term "gelatin" refers to a solid or semi-solid substance extracted from collagen-containing connective tissue of multicellular animals (metazoans). Collagen proteins, herein collectively referred to as "collagen", have a structural function in the extracellular matrix. Collagen proteins are known to occur not only in higher animals such as mammals but even in very primitive sea sponges.

Gelatin is an irreversibly hydrolyzed form of collagen proteins and is produced by partial hydrolysis of collagen extracted from skins, bones, cartilage, connective tissues, organs, and intestines. The chemical composition of gelatin is similar to that of collagen. Gelatin is formed when the natural molecular bonds between individual collagen strands are broken down into a form that rearranges more easily. Thus, gelatin melts when heated and solidifies when cooled again.

In the biotech industry, a number of enzymes for use in pharmaceutical processes are produced in large-scale fermentation processes. Examples include *C. histolyticum* collagenase enzymes for the dissociation of organ tissue and the subsequent isolation of target cells from the dissociated organ tissue. Because the microbial culture producing the enzymes takes up components from the growth medium, it is desirable to develop media with peptones and extracts free of mammalian pathogenic agents. There is a particular safety-related concern regarding prions and bovine spongiform encephalopathy (BSE).

The drug substance of the invention, for injectable collagenase, consists of two microbial collagenases, referred to as Collagenase ABC I and Collagenase ABC II. It is understood that the terms "Collagenase I", "ABC I", and "collagenase ABC I" mean the same and can be used interchangeably. Similarly, the terms "Collagenase II", "ABC II", and "collagenase ABC II" refer to the same enzyme and can also be used interchangeably. These collagenases are secreted by bacterial cells. They are isolated and purified from *Clostridium histolyticum* culture supernatant by chromatographic methods. Both collagenases are special proteases and share the same EC number (E.C 3.4.24.3).

Collagenase ABC I has a single polypeptide chain consisting of approximately 1000 amino acids with a molecular weight of 115 kDa. Collagenase ABC II has also a single polypeptide chain consisting of about 1000 amino acids with a molecular weight of 110 kDa.

Even though the literature indicates that there are sequence homologies in regions of collagenase ABC I and ABC II, the two polypeptides do not seem to be immunologically cross reactive as indicated by the western blot analysis.

A first step in the method of the present invention may be the preparation of meat-free or vegetable-derived clostridia cell bank. Preferably, the *Clostridium histolyticum* is removed from a meat medium and resuspended in a medium containing a vegetable peptone and optionally yeast extract. An exemplary, albeit non-limiting, example of the steps involved in the preparation of an animal material-free clostridia cell bank is as follows:

| | |
|---|---|
| Step 1 | Starting cells: *Clostridium histolyticum* ATCC 21000, strain 004 in meat-derived medium; |
| Step 2 | Inoculate 1 mL of step 1 into 300 mL of media #1; |
| Step 3 | Incubate step 2 for 24 hours at 37° C. (1$^{st}$ culture); |
| Step 4 | Transfer 3 mL of step 3 (1$^{st}$ culture) to 1000 mL of media #1; |
| Step 5 | Incubate step 4 for 16 hours at 37° C. (2$^{nd}$ culture); |

| Step 6 | Centrifuge the $2^{nd}$ culture; |
|---|---|
| Step 7 | Re-suspend the pellet with the 5 mL of media #1 and 5 mL of 20% glycerol; |
| Step 8 | Freeze the aliquot of cells gradually; |
| Step 9 | Store the aliquot at −80° C. |

Once an animal material-free cell bank is established, the clostridia can be grown or fermented in various media, preferably vegetable-derived medium. The medium can optionally contain yeast extract. Exemplary, albeit non-limiting examples of such media are media designated M#1-#4 below. In addition, an exemplary, albeit non-limiting example of the steps of the fermentation process are as follows:

| Step 1 | Starting cells: Animal material free clostridia cell bank |
|---|---|
| Step 2 | Inoculate 1 mL of step 1 into the 300 mL of media #1; |
| Step 3 | Incubate step 2 for 16 to 24 hours at 37° C. ($1^{st}$ culture); |
| Step 4 | Transfer 10 mL of step 3 ($1^{st}$ culture) and 10 mL Vitamin/Mg solution to 1000 mL of media # 3, or 4 respectively; |
| Step 5 | Incubate step 4 for about 22 hours at 37° C. ($2^{nd}$ culture); |
| Step 6 | $2^{nd}$ culture for downstream isolation and purification. |

After preparation of "$2^{nd}$ culture", the collagenase I and collagenase II can be isolated and purified using any method capable of producing each enzyme separately to at least 95% purity. The method may combine one or more of the steps of ammonium sulfate precipitation, dialysis, hydroxylapatite (HA) chromatography, gel filtration and ion-exchange, preferably in that order. The gel filtration is preferably SEPHADEX G-75 gel filtration. The ion-exchange is preferably anion-exchange: Q-SEPHAROSE chromatography. In addition, when the clostridia have been preferably cultured in medium containing less glucose and more salt, the use of protease inhibitors such as leupeptin is not required. An exemplary, albeit non-limiting example of the isolation and purification steps for collagenase I and collagenase II are as follows:

| Stages of Product | Operations |
|---|---|
| Fermentation broth | Centrifugation or 1.0 μm filtration; |
| Clarified fermentation broth | Add ammonium sulfate (590 g/liter) and followed by centrifugation; |
| Crude Collagenase Precipitate | Dissolve Crude Collagenase Precipitate by adding purified water; |
| Crude collagenase solution | Note: can be stored at −20° C.; Dialyze crude collagenase solution against purified water overnight with 10 kDa pore size dialysis membrane; |
| Dialyzed crude collagenase | Clarify the dialyzed crude collagenase solution with either centrifugation or filtration or the combination of both; |
| Clarified solution | Add potassium phosphate buffer, pH 6.7 to a final concentration of 0.1M; |
| Collagenase in phosphate buffer | Load Collagenase solution to a hydroxylapatite (HA) column and elute the column using a gradient elution of increasing potassium phosphate concentration at ambient temperature (20° C.); |
| Collagenase HA eluate | Concentrate the eluate with ultrafiltration (30 kDa of pore size); |
| Concentrated collagenase | Load the concentrate onto a G75 gel filtration column at ambient temperature (20° C.) and elute with 20 mM Tris/150 mM NaCl; |
| Collagenase | Dialyze the eluate against a buffer (10 mM Tris, |
| G75 eluate | 3 mM calcium chloride ($CaCl_2$), pH 8.0) overnight; |
| Dialyzed G75 eluate | Load the dialyzed eluate on to a Q-Sepharose anion-exchange column at ambient temperature (20° C.) and elute using a gradient of 10 mM Tris HCl, 3 mM $CaCl_2$, pH 8.0 Buffer and 10 mM Tris HCl, 3 mM $CaCl_2$, 1M NaCl, pH 8.0 Buffer; |
| Collagenase class I fraction Collagenase class II fraction | Store them separately at −20° C. |

According to the invention, the peptone in the nutrient composition is an animal material-free derived peptone. In a preferred embodiment of the invention, the peptone is a plant product. Even more preferred, the peptone is from a plant source selected from the group consisting of soy bean, broad bean, pea, potato, and a mixture thereof. The peptone may be selected from the group consisting of OXOID VG100 Vegetable peptone No. 1 from pea (VG100), OXOID VG200 Vegetable peptone phosphate broth from Pea (OXOID VG200), MERCK TSB CASO-Bouillion animal-free (TSB), INVITROGEN Soy bean peptone No 110 papainic digest (SP6), FLUKA Broad bean peptone (BP), Organotechnie Plant peptone E1 from potato (E1P), BBL Phytone™ peptone and BD DIFCO Select Phytone™.

Regarding configuration of the nutrient medium and peptone concentration in particular, the composition according to the invention may comprise two or more different peptones, whereby the aggregate concentration of the plant peptones in the composition is between about 2% and about 15% weight by volume. Even more preferred, the aggregate concentration of the plant peptones in the composition is between about 5% and about 12% weight by volume, preferably about 10% weight by volume.

In a preferred embodiment of the invention, a single type of peptone is present in the nutrient composition of the invention, whereby the peptone is selected from the group consisting of BP, E1P, Soy bean peptone E110, OXOID VG100, and OXOID VG200, and whereby the concentration of the peptone in the composition is about 5% weight by volume. In yet another very much preferred embodiment of the invention, a single type of peptone is present in the nutrient composition of the invention, whereby the peptone is BBL phytone peptone or DIFCO Select Phytone™ UF, and whereby the concentration of the peptone in the composition is about 10-13% weight by volume.

In another preferred embodiment, the nutrient composition may contain 0.5-5% yeast extract, more preferably about 1-4%, and most preferably about 1.5-2.5%. Yeast extract is available from a variety of suppliers, including COLE-PARMER (Vernon Hills, Ill.) and FISHER SCIENTIFIC (Pittsburgh, Pa.).

In yet a preferred embodiment of the invention, the pH of the media is between pH 7 and pH 8. Even more preferred is a pH between about pH 7.2 and about pH 7.7, most preferably about 7.4.

In a further preferred embodiment, the media according to the invention are sterilized, that is to say the composition is made free of any self-replicating organism. Sterilization can be achieved by standard methods known to the skilled person, e.g., by heat treatment such as autoclaving.

The media compositions according to the invention are particularly useful for cultivating *Clostridium histolyticum* bacteria. A preferred embodiment of the invention is therefore a composition according to the invention additionally comprising an inoculum of *Clostridium histolyticum* bacteria in a medium composition of the invention.

In another embodiment, the present invention provides a drug substance, wherein the drug substance has at least one specification selected from table A below:

TABLE A

| Test | Specification ABC-I | ABC-II |
|---|---|---|
| Appearance | Clear colorless and essentially free from participate matter | |
| Endotoxin | <10 EU/mL | |
| Identity (and purity) by SDS-PAGE (Reduced conditions, Coomasie) | Major collagenase band between 98-188 kDa ≥95% | Major collagenase band between 97-200 kDa ≥95% |
| SRC assay (ABC -I) | 1967-3327 SRC units/mg | NA |
| GPA assay (ABC-II) | NA | 81934-119522 GPA units/mg |
| Analysis of Proteins HPLC System (Aggregation by size exclusion chromatography) | ≥98% main peak; ≤2% aggregates by area | |
| Identity and purity by reverse phase liquid chromatography | Major peak (ABC I or ABC II), ≥95% by area; Retention times of ABC-I and ABC-II within 5% of reference | |
| Clostripain assay (BAEE assay) | ≤1 U/mg | |
| Bioburden | <1 cfu/mL | |

Such drug product of the invention is useful for the treatment of collagen-mediated disease. Examples of such collagen mediated-diseases that may be treated by the compositions and methods of the invention include but are not limited to: Dupuytren's disease; Peyronie's disease; frozen shoulder (adhesive capsulitis), keloids; tennis elbow (lateral epicondylitis); scarred tendon; glaucoma; herniated discs; adjunct to vitrectomy; hypertrophic scars; depressed scars such as those resulting from inflammatory acne; post-surgical adhesions; acne vulgaris; lipomas, and disfiguring conditions such as wrinkling, cellulite formation and neoplastic fibrosis. U.S. Pat. No. 6,086,872, incorporated herein by reference in its entirety, discloses the use of collagenase preparations in the treatment of Dupuytren's disease. U.S. Pat. No. 6,022,539, incorporated herein by reference in its entirety, discloses the use of collagenase preparations in the treatment of Peyronie's disease. U.S. patent application Ser. No. 12/266,090, incorporated herein by reference in its entirety, discloses the treatment of adhesive capsulitis with purified preparations of collagenase. U.S. patent application Ser. No. 11/703,269, incorporated herein by reference in its entirety, discloses the treatment of cellulite with purified preparations of collagenase. U.S. Pat. Nos. 7,824,673 and 6,958,150, incorporated herein by reference in their entirety, discloses the treatment of adipose tissue with purified preparations of collagenase. U.S. Pat. No. 7,854,929, incorporated herein in its entirety, discloses the treatment of lateral epicondylitis using purified preparations of collagenase.

In addition to its use in treating collagen-mediated diseases, the composition of the invention is also useful for the dissociation of tissue into individual cells and cell clusters as is useful in a wide variety of laboratory, diagnostic and therapeutic applications. These applications involve the isolation of many types of cells for various uses, including microvascular endothelial cells for small diameter synthetic vascular graft seeding, hepatocytes for gene therapy, drug toxicology screening and extracorporeal liver assist devices, chondrocytes for cartilage regeneration, and islets of Langerhans for the treatment of insulin-dependent diabetes mellitus. Enzyme treatment works to fragment extracellular matrix proteins and proteins which maintain cell-to-cell contact. Since collagen is the principle protein component of tissue ultrastructure, the enzyme collagenase has been frequently used to accomplish the desired tissue disintegration. In general, the composition of the present invention is useful for any application where the removal of cells or the modification of an extracellular matrix, are desired.

Collagenase compositions of the invention may also be prepared by mixing either a specific number of activity units or specific masses of the preferably purified enzymes. Collagenase activity can be measured by the enzyme's ability to hydrolyze either synthetic peptide or collagen substrate. Those skilled in the art will recognize that enzyme assays other than those disclosed herein may also be used to define and prepare functionally equivalent enzyme compositions.

Another aspect of the present invention is the reproducible optimization of the mass ratio of collagenase I to collagenase II in the composition of the invention. The reproducibility of the ratio of collagenase I to collagenase II has previously been a challenge because of several factors. Commercial fermentation of *Clostridium* can result in a 1 to 2 ratio of collagenase I and collagenase II. By separately purifying collagenase I and collagenase II, and recombining them at an optimized fixed mass ratio, the present invention maximizes the synergistic activity provided by the two different collagenases resulting in superior therapeutic benefit.

The invention also provides pharmaceutical formulations of the compositions of the invention. The pharmaceutical formulations of the present invention comprise a therapeutically effective amount of a collagenase composition of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, perfuming agents, preservatives and antioxidants can also be present in the composition, according to the judgment of the formulator.

The pharmaceutical compositions of this invention may be administered parenterally, topically, or via an implanted reservoir. The term parenteral as used herein includes subcutaneous, intracutaneous, intravenous, intramuscular, intraarticular, intraarterial, intrasynovial, intrasternal, intrathecal, intralesional and intracranial injection or infusion techniques. In a preferred embodiment, the composition is injected into the disfiguring tissue. In the case of Peyronie's or Duputyren's diseases or adhesive capsulitis, the composition is injected into the cord or plaque. The term "local administration" is defined herein to embrace such direct injection. U.S. Pat. Nos. 5,393,792 and 5,422,103, incorporated herein by reference in their entirety, disclose compositions of collagenase used for topical administration to burn sites.

Furthermore, particularly good results can be obtained by immobilizing the site of injection after administration. For example, the site of administration can be immobilized for 4 or more hours.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The sterile solutions may also be lyophilized for later use.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In one preferred embodiment, the drug substance of the invention is a lyophilized injectable composition formulated with lactose. A preferred collagenase composition comprising a mixture of collagenase I and collagenase II has a specific activity of at least about 700 SRC units/mg, such as at least about 1000 SRC units/mg, more preferably at least about 1500 SRC units/mg. One SRC unit will solubilize rat tail collagen into ninhydrin reaction material equivalent to 1 nanomole of leucine per minute, at 25° C., pH 7.4.

Collagenase has been described in ABC units as well. This potency assay of collagenase is based on the digestion of undenatured collagen (from bovine tendon) at pH 7.2 and 37 degrees C. for 20-24 hours. The number of peptide bonds cleaved is measured by reaction with ninhydrin. Amino groups released by a trypsin digestion control are subtracted. One net ABC unit of collagenase will solubilize ninhydrin reactive material equivalent to 1.09 nanomoles of leucine per minute. One SRC unit equal approximate 6.3 ABC unit or 18.5 GPA unit.

In another embodiment, each milligram of injection collagenase preferably has approximately 2800 SRC units measured with a potency assay using soluble rat tail collagen as the substrate, and 51000 units measured with a potency assay using a synthetic substrate, pzGPGGPA.

In another preferred embodiment, the collagenase composition of the invention is a lyophilized injectable composition formulated with Sucrose, Tris at a pH level of about 8.0. Most preferably, 1.0 mg of the drug substance of the invention is formulated in 60 mM Sucrose, 10 mM Tris, at a pH of about 8.0 (this equates to 20.5 mg/mL of sucrose and 1.21 mg/mL of Tris in the formulation buffer). Examples of some of the formulations include, but not limited to: for a 0.9 mg of the drug substance dose, 18.5 mg of sucrose and 1.1 mg of Tris are added in each vial, where the targeting a vial fill volume is 0.9 mL; and for a 0.58 mg of the drug substance dose, 12.0 mg sucrose (multicompendial) and 0.7 mg of Tris (multicompendial).

In accordance with the invention, methods are provided for treating collagen-mediated diseases comprising the step of administering to a patient in need thereof, a therapeutically effective amount of a composition of the invention, or a therapeutically effective amount of a pharmaceutical formulation of the invention. By a "therapeutically effective amount" of a compound of the invention is meant an amount of the compound which confers a therapeutic effect on the treated subject, at a reasonable benefit/risk ratio applicable to any medical treatment.

The therapeutic effect may be objective (i.e., measurable by some test or marker) or subjective (i.e., subject gives an indication of or feels an effect). Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

In yet more detail, the present invention is described by the following items which represent preferred embodiments thereof.

1. A method for preparing a drug product comprising isolated and purified collagenase I and collagenase II having the sequence of *Clostridium histolyticum* collagenase I and collagenase II, said method including the steps of:
    a) fermenting *Clostridium histolyticum* in an animal-derived material-free medium to obtain a crude collagenase mixture, wherein said medium is treated in one or more of the following ways: (1) decreasing the glucose content in the animal-derived material-free medium; and (2) increasing the salt concentration in the animal-derived material-free medium;
b) purifying collagenase I and collagenase II separately from the crude collagenase mixture; and
c) recombining the purified collagenase I and collagenase II at an optimized fixed mass ratio;
wherein said drug product is at least 95% pure and substantially free of any contaminating proteases.

2. The method of Item 1, wherein the animal-derived material-free medium comprises vegetable-derived peptone.
3. The method of Item 1, wherein the animal-derived material-free medium comprises soybean-derived peptone.
4. The method of Item 1, wherein the optimized fixed mass ratio of collagenase I to collagenase II is 0.5 to 1.5.
5. The method of Item 1, wherein the optimized fixed mass ratio of collagenase I to collagenase II is 1.
6. The method of Item 1, wherein the collagenases are 95% pure.
7. The method of Item 6, wherein the collagenases are 98% pure.
8. The method of Item 1, wherein the purity is determined by one or more of the following: sodium dodecyl sulfate polyacrylamide gel electrophoresis (SDS-PAGE), high performance liquid chromatography (HPLC), reverse-phase HPLC, or enzymatic assays.
9. The method of Item 1, wherein the drug product is essentially clostripain-free.
10. The method of Item 1, wherein step (b) comprises:
  i. ammonium sulfate precipitation;
  ii. dialysis;
  iii. hydroxylapatite (HA) chromatography;
  iv. gel filtration chromatography; and
  v. anion exchange chromatography.
11. The method of Item 11, wherein steps (i), (ii), (iii), (iv) and (v) are performed in order.
12. The method of Item 11, wherein the column used for chromatography is a hydroxylapatite (HA) column.
13. The method of Item 11, wherein the gel filtration is SEPHADEX G-75 gel filtration.
14. The method of Item 11, wherein the anion-exchange is Q-SEPHAROSE anion-exchange.
15. The method of Item 1, wherein the purification is performed in the absence of leupeptin.
16. The method of Item 1, further including preparing an animal material-free clostridia cell bank.
17. The method of Item 1, wherein the glucose content in the animal material-free medium is less than about 5 g/L.
18. The method of Item 1, wherein the glucose content in the animal material-free medium is less than about 2 g/L.
19. The method of Item 1, wherein the glucose content in the animal material-free medium is essentially zero.
20. The method of Item 1, wherein the salt content in the animal material-free medium is greater than about 5 g/L.
21. The method of Item 1, wherein the salt content in the animal material-free medium is greater than about 7.5 g/L.
22. The method of Item 1, wherein the salt content in the animal material-free medium is greater than about 9 g/L.
23. A drug product prepared by the method of any of Items 1-23.
24. A medium for the fermentation of *Clostridium histolyticum* including:
  a. Phytone or VEGGIETONE (vegetable peptone);
  b. yeast extract; and
  c. less than about 5 g/L glucose;
  wherein the pH of said medium is 7.2-7.7.
25. A medium for the fermentation of *Clostridium histolyticum* comprising:
  a. phytone or VEGGIETONE (vegetable peptone)
  b. yeast extract; and
  c. greater than about 5 g/L salt;
  wherein the pH of said medium is 7.2-7.7.
26. The medium of Item 26, wherein the salts are selected from the group consisting of potassium phosphate, sodium phosphate, sodium chloride, and magnesium sulfate.
27. The medium of any one of Items 25-27, further comprising one or more vitamins selected from the group consisting of ferrous sulfate, riboflavin, niacin, calcium pantothenate, pimelic acid, pyridoxine hydrochloride and thiamine hydrochloride.
28. The medium of Item 25, wherein the pH of said medium is 7.4.
29. A method for treating a patient suffering from a collagen-mediated condition or disease, comprising administering to said patient a therapeutically effective amount of the drug product of Item 24.
30. The method of Item 30, wherein said condition or disease is Dupuytren's disease, Peyronie's disease, frozen shoulder (adhesive capsulitis), tennis elbow (lateral epicondylitis), keloids, scarred tendon, glaucoma, herniated discs, adjunct to vitrectomy, hypertrophic scars, depressed scars, post-surgical adhesions, acne vulgaris, lipomas, wrinkling, cellulite formation or neoplastic fibrosis.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compositions and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

Example 1

Preparation of an Animal Material Free Cell Bank

The starter cell culture was *Clostridium histolyticum* ATCC 21000, strain 004, which was originally created with bovine-derived materials. The cells were first grown in animal material free medium (M #1, Table 1). Briefly, the recipe includes: phytone, 51.5 g, yeast extract 8.5 g, 1000 mL water. The pH was adjusted to 7.30 with NaOH, and sterilized at 121° C. for 20 min. 1 mL of the starting material was then inoculated into 300 mL of medium #1 and incubated for 24 hours at 37° C. ($1^{st}$ culture). 3 mL of the $1^{st}$ culture was transferred to 1000 mL of medium #1 and incubated for 16 hours ($2^{nd}$ culture). The $2^{nd}$ culture was then centrifuged aseptically. The pellet was re-suspended with 5 mL medium #1 and 5 mL 20% glycerol. The aliquots of cell suspension were frozen gradually and stored at −80° C.

Example 2

Fermentation Process

*Clostridium histolyticum* ATCC 21000, strain 004 was inoculated into the starting culture with medium #1 or #2 and incubated at 37° C. for 16 hr. 10 mL of the starting culture (M#1 or #2) and 10 mL Mg/vitamin solution (Example 3) was then transferred to each liter of M#3 or #4 or any variation to either M#3 or M#4 specified in the examples and incubated for 22 hours. *Clostridium histolyticum* grew well with the $OD_{600}$ reaching >2.5.

TABLE 1

Media recipes and preparation

| | M #1 | M #2 | M #3 | M #4 |
|---|---|---|---|---|
| Phytone | 15.45 g | | 103 g | |
| VEGGIETONE (vegetable peptone) | | 15.45 g | | 103 g |
| Yeast extract | 2.55 g | 2.55 g | 17 g | 17 g |
| KH2PO4 | | | 1.92 g | 1.92 g |
| K2HPO4 | | | 1.25 g | 1.25 g |
| Na2HPO4 | | | 3.5 g | 3.5 g |
| NaCl | | | 2.5 g | 2.5 g |
| vol of water | 0.3 L | 0.3 L | 1 L | 1 L |

Example 3

Preparation of MgSO4/VF Solution

The solution was prepared separately, by dissolving 8 g $MgSO_4$, 1.2 g ferrous sulfate, 0.05 g riboflavin, 0.1 g Niacin, 0.1 g Calcium pantothenate, 0.1 g pimelic acid, 0.1 g pyridoxine, and 0.1 g thiamine in 1100 mL water. The solution was sterilized with 0.22 um filtration.

Example 4

Fermentation Medium Study: Effect of Glucose and Salt

SDS-PAGE Analysis

The M#3 medium was modified with additional components as described in Table 2. The fermentation broths were analyzed by SDS-PAGE.

TABLE 2

Formation Modifications

| Medium modification | Glucose | Remove salt | Additional Yeast extract |
|---|---|---|---|
| M #3 | No | No | No |
| M #3 + additional yeast extract | No | No | 33 g/L |
| M #3 − salt | No | Yes | No |
| M #3 + glucose | 10 g/L | No | No |
| M #3 − salt + glucose | 10 g/L | Yes | No |

Salt: KH2PO4, K2HPO4, Na2HPO4, NaCl as described in Table 1.

Figure 1:
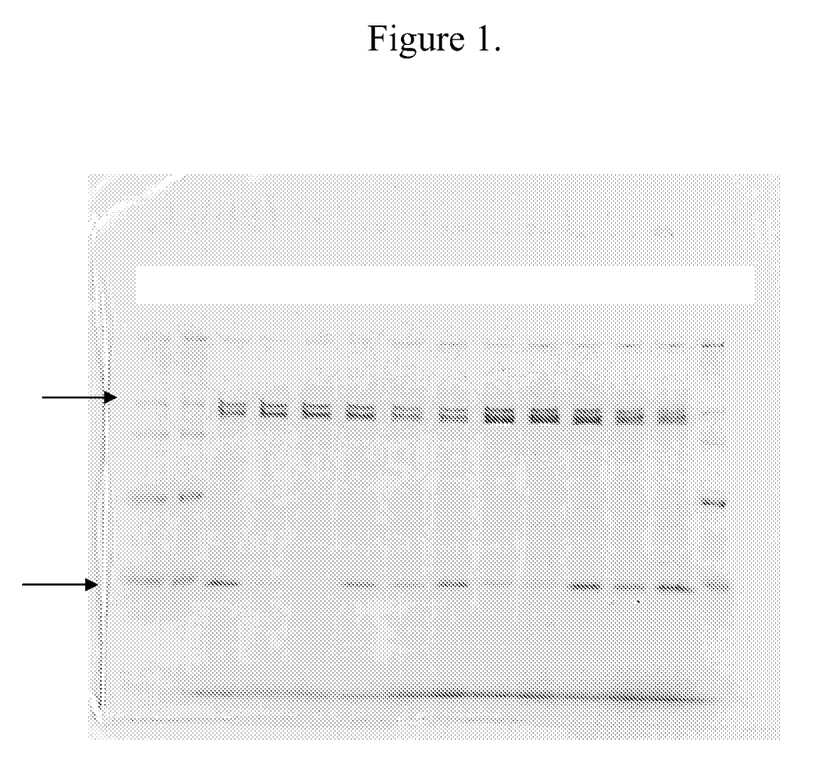
FIG. 1 is a photomicrograph of an SDS-PAGE gel showing the results of an experiment comparing media with and without glucose or salt. The double band indicated by the upper arrow is collagenase I and II. The band indicated by the lower arrow is clostripain. The protein samples of each lane are identified as follows.

FIG. 1 shows the results of an SDS-PAGE analysis of culture supernatants grown in the presence or absence of salt and the presence or absence of glucose. FIG. 1 shows that fermentation with glucose (lane 7) increases the production of clostripain (the 43 kDa band) when compared to fermentation without glucose (lane 4).

FIG. 1 also shows that clostripain production increases drastically when fermentation occurs in the absence of salt (lanes 6, 8, 11 and 13) compared to fermentation in the presence of salt (lanes 4 and 9; notice the more prominent 43 kDa band).

Casein Assay

It was also shown through a caseinase assay that glucose in media increases the production of proteolytic enzymes that contribute to the degradation of collagenase. The caseinase assay is commonly used to measure general proteolytic activity by assaying the proteolytic degradation of the substrate casein. The fermentation broths from M #3 with and without glucose were processed with ammonium sulfate and the precipitates were analyzed for caseinase activity (exp: 1325). For M #3 with glucose, the precipitate showed activity of 80.0 unit per unit of cell density (OD600). The precipitate from M #3 without glucose, showed activity of 60.5 unit per unit of cell density. Thus, the glucose growth condition displayed 32% more caseinase activity. Higher caseinase activity is consistent with the presence of clostripain and may contribute to increased degradation of collagenase.

Example 5

Figure 2:
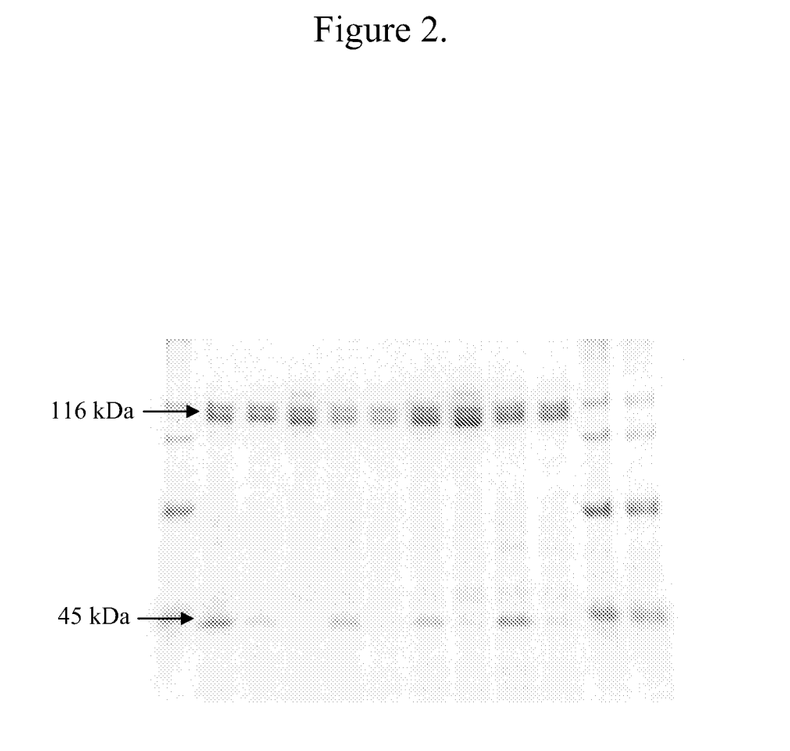
FIG. 2 is a photomicrograph of an SDS-PAGE gel showing the results of an experiment using phytone and VEGGIETONE (vegetable peptone) media with and without glucose. The double band indicated by the upper arrow is collagenase I and II; the band indicated by the lower arrow is clostripain. The protein samples of each lane are identified as follows.

Fermentation Medium Study: VEGGIETONE (Vegetable Peptone) Vs. Phytone with and without Glucose Cultures of *C. histolyticum* were grown in phytone-based and VEGGIETONE (vegetable peptone)-based media, with and without added glucose. FIG. 2 shows the results of an SDS-PAGE analysis of the protein isolated from the cultures.

A comparison of proteins derived from cells grown in phytone and VEGGIETONE (vegetable peptone) (lane 7 and 8) revealed that VEGGIETONE (vegetable peptone) produced much less clostripain. Additionally, a comparison of proteins derived from cells grown in phytone with glucose (lanes 5 and 9) and phytone without glucose (lanes 3 and 7) revealed that the use of media with glucose drastically increased the production of clostripain compared to media without glucose. In contrast, VEGGIETONE (vegetable peptone) medium without glucose did not display the same effect. A comparison of proteins derived from cells grown in VEGGIETONE (vegetable peptone) with glucose (lanes 6 and 10) and VEGGIETONE (vegetable peptone) without glucose (lanes 4 and 8) indicates that the addition of glucose to VEGGIETONE (vegetable peptone), did not drastically increase clostripain production. However, this may be explained by the presence of salt in the VEGGIETONE (vegetable peptone) medium. (See example 6).

Moreover, the VEGGIETONE (vegetable peptone)-derived protein sample revealed a consistent phenomenon: some collagenase class I precursor did not fully convert to mature collagenase class I. The conversion process continued after ammonium sulfate precipitation, and completed before the ion exchange column.

Yield: approximately 20 mg/L broth for either ABC I or II.

Example 6

Fermentation Medium Study: VEGGIETONE (Vegetable Peptone) and Salt

Figure 3:
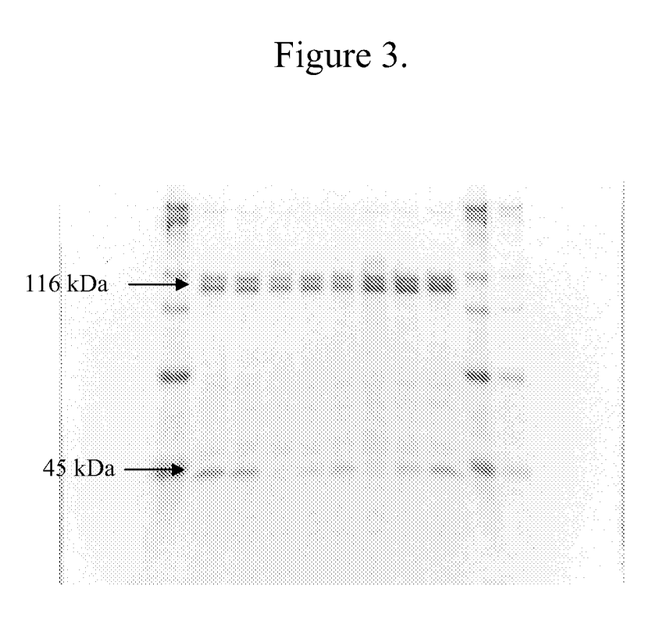
FIG. 3 is a photomicrograph of an SDS-PAGE gel showing the results of an experiment using various VEGGIETONE (vegetable peptone) media formulations with and without salt. The double bands indicated by the upper arrow are the collagenases I and II; the band indicated by the lower arrow is clostripain. The protein samples of each lane are identified as follows.

Clostripain levels were measured in protein samples derived from *C. histolyticum* cultures grown in media prepared with and without salt. Cells were grown in VEGGIETONE (vegetable peptone) medium with salt, VEGGIETONE (vegetable peptone) medium without salt and with $CaCl_2$, phytone growth medium or 5% VEGGIETONE (vegetable peptone) medium with $CaCl_2$ (disclosed in U.S. patent application Ser. No. 12/478,306). FIG. 3 reveals that clostripain (43 kDa band) production was drastically reduced in cultures grown in VEGGIETONE (vegetable peptone) with salt (lanes 4 and 7) compared to growth in VEGGIETONE (vegetable peptone) without salt (lanes 5 and 8). Protein samples derived from cultures grown in phytone (lanes 6 and 9) or 5% VEGGIETONE (vegetable peptone) and 1 mM CaCl2 (lane 3) also displayed increased production of clostripain compared to VEGGIETONE (vegetable peptone) with salt.

Example 7

The Isolation and Purification Process

After fermentation in medium #4, the Clostridia cells were removed by centrifugation or 1 μm filtration. Ammonium sulfate (590 g/liter) was added to the clarified fermentation solution to precipitate out the collagenases. The Collagenase Precipitation was recovered by centrifugation, reconstituted with purified $diH_2O$ and dialyzed against purified $diH_2O$ for at least 14 hours.

The dialyzed, Crude Collagenase solution was centrifuged at 20,000 g for 15 minutes at 2-8° C., the supernatant was filtered through a 0.22 μm nitrocellulose membrane and the filtered solution was adjusted to 0.1 M potassium phosphate (KPi) by adding 0.4 M KPi, pH 6.7 Buffer. This diluted Collagenase solution was then run through a 185 mL hydroxylapatite (HA) column and the collagenase was eluted using a gradient of increasing potassium phosphate concentration at ambient temperature (20° C.). The hydroxylapatite column captured collagenase while allowing all the non-collagenase material to go through the flow-through fraction. In addition, the gradient elution also helped to partially remove DNA impurities.

The resulting collagenase fractions were pooled, concentrated with 30 kDa ultrafiltration, and loaded onto a SEPHADEX G-75 gel filtration column at ambient temperature (20° C.). The collagenase was eluted with 20 mM Tris/150 mM NaCl. The collagenase fractions were pooled and dialyzed against buffer A (10 mM Tris, 3 mM calcium chloride ($CaCl_2$), pH 8.0. The dialyzed collagenase pool was then filtered through a 0.22 μm nitrocellulose filter.

The filtered collagenase in Tris Buffer solution was then run through a Q-SEPHAROSE anion-exchange column at ambient temperature (20° C.) and eluted using a gradient of 10 mM Tris HCl, 3 mM $CaCl_2$, pH 8.0 Buffer and 10 mM Tris HCl, 3 mM $CaCl_2$, 1 M NaCl, pH 8.0 Buffer. The Q-SEPHAROSE column helped to separate Collagenase ABC I from Collagenase ABC II in addition to removing residual DNA impurities and endotoxins. The peak fractions for Collagenase ABC I and ABC II were collected and pooled separately and stored at −20° C.

In comparison to the methods disclosed in U.S. Pat. No. 7,811,560 in which cells were grown in the presence of phytone and glucose, the currently claimed method utilizes VEGGIETONE (vegetable peptone) growth medium without additional glucose. The currently claimed methods result in the surprising reduction in the production of clostripain. When proteases are present in a crude collagenase mixture, skilled artisans must make use of protease inhibitors, such as leupeptin, and must perform purification steps in specially designed cold rooms with chilled solutions. The currently claimed method drastically reduces the amount of clostripain produced, thus eliminating the need for adding protease inhibitors, such as leupeptin to the reagents and solutions and further allowing a researcher to conduct all purification steps at ambient temperature.

Example 8

BAEE Assay of Clostripain Activity

Clostripain activity was analyzed using an enzymatic assay that uses N-a-Benzoyl-L-Arginine Ethyl Ester (BAEE) as a substrate. The enzyme was activated with 2.5M DTT prior to being mixed with BAEE. The rate of BAEE breakdown was measured by spectrophotometer at 253 nm, Light path=1 cm. Assay conditions: T=25° C., pH=7.4, 0.75 mM BAEE. One unit of enzyme can hydrolyze 1.0 mole of BAEE per minute. The results are shown in Table 4. The results of the BAEE assay show that clostripain activity was drastically reduced in collagenase preparations derived from those cultures that were grown in VEGGIETONE (vegetable peptone) when compared to collagenase preparations derived from cultures grown in phytone.

TABLE 4

| Growth condition | Activity (U/mg) |
| --- | --- |
| Collagenase I + II from Phytone | 15.973 |
| Collagenase ABC I + II from bovine materials Batch 1 | 0.25 |
| Collagenase ABC I + II from bovine materials Batch 2 | No activity |
| Collagenase ABC I from Veggietone batch 1 | No activity |
| Collagenase ABC II from Veggietone batch 1 | 0.08 |
| Collagenase ABC I from Veggietone batch 2 | No activity |
| Collagenase ABC II from Veggietone batch 2 | No activity |

Example 9

Collagenase Assay Method 1: SRC Assay

The soluble rat tail collagen (SRC) assay uses soluble rat tail collagen as a substrate to measure collagenase activity (Mallya S K et al., Anal. Biochem., 158, 334-345). This assay procedure consists of two major parts: 1) the enzymatic reaction involving the digestion of rat tail tendon collagen by collagenase and; 2) the subsequent measurement of liberated peptide fragments/amino acids with ninhydrin reagent.

Method:

Collagenase was incubated for 2.5 hours with soluble rat tail collagen. The extent of collagen breakdown was determined using the Moore and Stein (1948) colorimetric ninhydrin method. Amino acids liberated are expressed as micromoles leucine per milligram collagenase. One unit equals one micromole of L-leucine equivalents from collagen 2.5 hours at 25° C. and pH 7.4 under the specified conditions. One net collagenase unit will solubilize ninhydrin reaction material equivalent to 1 nanomole of leucine per minute.

Reagents:

10 mM HCl; 100 mM Tris(hydroxymethyl)aminomethane/20 mM calcium acetate, pH 7.4 at 25° C. (TC assay buffer); Enzyme buffer: 20 mM Tris(hydroxymethyl)aminomethane/4 mM calcium acetate, pH 7.4 at 25° C.; Collagen solution (2 mg/mL collagen in 10 mM HCl); 0.5 M HCl; Leucine standard assay solution (1 mM leucine); Rosen buffer: 2.6 M sodium acetate/0.2 mM sodium cyanide/1.1 M acetic acid; 3% Ninhydrin in 2-methoxyethanol; 50% Isopropanol.

Procedures:

Incubation: Collagenase was incubated with enzyme buffer, HCl, TC Assay buffer, and Collagen in a 25° C. water bath for 150 minutes.

Quenching: At the end of the incubation period, the reaction tubes were removed from the water bath, and 2 mL of 0.5 M HCl was added to quench the reaction.

Color Development and Reading: A 1 mL aliquot from each of the reaction tubes was transferred into the appropriately-labeled culture tubes. 0.5 mL Rosen buffer and 0.5 mL 3% ninhydrin were dispensed into each culture tube. The culture tubes were placed in a boiling water bath for 15 minutes, after which the tubes were removed from the boiling water bath, and 3 mL of 50% isopropanol was added. The tubes were allowed to cool for at least 20 minutes and the absorbances ($A_{570}$) of each culture tube were read and the readings recorded. The results are shown in Table 5.

Example 10

Collagenase Assay Method 2: GPA Assay

Carbobenzoxy-glycyl-L-prolyl-glycyl-glycyl-L-prolyl-L-alanine (zGPGGPA) is a synthetic substrate for Clostridial collagenase. This substrate is readily cleaved by Class II collagenases (collagenase ABC II) into the two peptides; carbobenzoxy-glycyl-L-prolyl-glycine (zGPG) and glycyl-L-prolyl-L-alanine (GPA). The released free amino group on GPA is reacted with ninhydrin reagent. The optical density of purple ninhydrin reaction solution is measured with spectrometer at 570 nm and compared with ninhydrin reaction from collagenase reference standard. The unit of collagenase activity was expressed as nmol leu equiv./min. The procedure is based on that of W. Appel (in H. U. Bergmeyer, ed., *Methods of Enzymatic Analysis*; New York: Academic Press/Verlag Chemie, 1974).

Solutions:

Appel's Tris buffer [0.05 M Tris (hydroxymethyl) aminomethane/0.1 M calcium acetate, pH 7.2; substrate solution [2 mg/mL (3.4 mM) zGPGGPA in Appel's Tris buffer]; Leucine standard assay solution (1 mM leucine); 0.5 M HCl; Rosen buffer (2.6 M sodium acetate/0.2 mM sodium cyanide/1.05 M acetic acid); 3% Ninhydrin; 50% Isopropanol.

Procedure 1.00 mL substrate solution was added into each reaction tube. The appropriate amount of buffer was added to each reaction tube. All tubes were placed in a water bath and collagenase was added to each pre-warmed reaction tube. After 10 minutes in the 25° C. water 0.50-mL aliquot was removed and transferred to the correspondingly labeled culture tube with 0.5 mL HCl.

Color Development and Reading: 0.5 mL Rosen buffer and 0.5 mL 3% ninhydrin were dispensed into each culture tube and the tubes were placed in a boiling water bath for 15 minutes. At the end of the boiling period, the tubes were removed from the boiling water bath, and 3 mL of 50% isopropanol was added to each tube. The tubes were allowed to cool for at least 20 minutes and the absorbances ($A_{570}$) of each culture tube were read and recorded. The results are displayed in Table 5.

Example 11

SDS-PAGE, SRC and GPA Analysis of the Post Q Column Collagenase

Purified aliquots of collagenase ABC I in Tris buffer stored at 4° C. for 0, 7 and 17 days were evaluated for biological activity using the SRC assay and for primary structure integrity using SDS-PAGE, Coomassie Brilliant Blue staining. Purified aliquots of collagenase ABC II in Tris buffer stored at 4° C. for 0, 7 and 17 days were evaluated for biological activity using the GPA assay and for primary structure integrity using SDS-PAGE, Coomassie Brilliant Blue staining. The results are shown in table 5.

TABLE 5

| Stability at 4° C. of the post Q column collagenase | | | | |
|---|---|---|---|---|
| | ABC I | | ABC II | |
| days | SRC U/mg | SDS-PAGE | GPA U/mg | SDS-PAGE |
| 0 | 3327 | — | 108038 | — |
| 7 | 3298 | Similar to 0 days | 109068 | Similar to 0 days |
| 17 | 3299 | Similar to 0 days | 105023 | Similar to 0 days |

The results of the SRC, GPA, and SDS-PAGE analyses surprisingly reveal that collagenase remains stable and active in solution even after being stored for as long as 17 days. There is no activity lost and no visible collagenase protein degradation. Such stability and lack of degradation would not be expected in samples that contained levels of clostripain and other contaminating proteases. Thus, it is clear from the collagenase and clostripain assays that the currently disclosed fermentation methods utilizing vegetable-based peptone with high salt and no glucose were superior to known methods in reducing clostripain levels in purified collagenase samples. This result is consistent with the clostripain test result in example 8.

Example 12

Comparison Between a Collagenase Reference Standard and Collagenase Purified from Medium #4 Culture (VEGGIETONE (Vegetable Peptone))

The purified collagenase I and II from M#4 were tested side by side with a collagenase reference standard.

TABLE 6

Test Results on collagenases purified from
VEGGIETONE (vegetable peptone) Medium (M#4)

| Test | Test Results | | |
|---|---|---|---|
| | Class I from M #4 | Class II from M #4 | I + II from M#4 |
| Identity by SDS-PAGE | Same as RS (110-115 kDa) | Same as RS (107-110 kDa) | Same as RS |
| Analysis by reverse phase HPLC | Same Retention time as Standard purity > 95% | Same Retention time as Standard purity > 95% | N/A |
| Identity by peptide map | Conforms to ref standard | Conforms to ref standard | N/A |
| SRC assay: specific activity | 2888 (1967-3327 units/mg) | N/A | 2784 (2441-3759 U/mg) |
| GPA assay: specific activity | N/A | 91279 (81934-119522 units/mg) | 57061 (42923-64384 U/mg) |
| Clostripain activity | No detectable activity | No detectable activity | N/A |

The results from Table 6 reveal that the collagenases purified according to the methods disclosed herein were comparable to a known reference standard collagenase with respect to their activity and stability.

The methods of the current invention provide a means for producing essentially clostripain-free preparations of collagenase, thus eliminating the need for using protease inhibitors, such as leupeptin. Furthermore, the elimination of detectable amounts of clostripain activity from the cultures allows researchers to perform the purification steps at ambient temperature.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for fermenting a clostripain-producing *Clostridium histolyticum* to obtain a mixture of collagenase I and collagenase II, comprising fermenting said clostripain-producing *Clostridium histolyticum* in medium comprising peptone, wherein the peptone is Oxoid VG100 Vegetable Peptone made from pea, or Oxoid VG200 Vegetable Peptone phosphate broth,
    wherein said mixture of collagenase I and collagenase II is separately purified in the absence of added protease inhibitor and recombined to produce a drug product at least 95% pure as determined by reverse phase high performance liquid chromatography and contains no detectable clostripain activity using an enzymatic assay with N-a-Benzoyl-L-Arginine Ethyl Ester (BAEE) as substrate.

2. The method of claim 1, wherein the medium comprises greater than about 5 g/L total salt.

3. The method of claim 2, wherein the salt content in the medium is greater than about 7.5 g/L.

4. The method of claim 1, wherein the collagenase I and collagenase II are recombined at an optimized fixed mass ratio of 0.5 to 1.5.

5. The method of claim 4, wherein the optimized fixed mass ratio of collagenase I to collagenase II is 1.

6. The method of claim 1, wherein the collagenases are 97% pure.

7. The method of claim 1, wherein the collagenases are 98% pure.

8. The method of claim 1, wherein the purifying comprises:
    i. ammonium sulfate precipitation;
    ii. dialysis;
    iii. hydroxylapatite chromatography;
    iv. gel filtration; and
    v. anion exchange.

9. The method of claim 8, wherein steps (i), (ii), (iii), (iv) and (v) are performed in order.

10. The method of claim 1, wherein the clostripain-producing *Clostridium histolyticum* is ATCC 21000.

11. A method for fermenting a clostripain-producing *Clostridium histolyticum* to obtain a mixture of collagenase I and collagenase II, comprising fermenting said clostripain-producing *Clostridium histolyticum* in medium comprising peptone and lacking glucose, wherein the peptone is BBL Phytone Peptone, or BD Difco Select Phytone,
    wherein said mixture of collagenase I and collagenase II is separately purified in the absence of added protease inhibitor and recombined to produce a drug product at least 95% pure as determined by reverse phase high performance liquid chromatography and contains no detectable clostripain activity using an enzymatic assay with N-a-Benzoyl-L-Arginine Ethyl Ester (BAEE) as substrate.

12. The method of claim 11, wherein the collagenase I and collagenase II are recombined at an optimized fixed mass ratio of 0.5 to 1.5.

13. The method of claim 12, wherein the optimized fixed mass ratio of collagenase I to collagenase II is 1.

14. The method of claim 11, wherein the collagenases are 97% pure.

15. The method of claim 14, wherein the collagenases are 98% pure.

16. The method of claim 11, wherein the purifying comprises:
    i. ammonium sulfate precipitation;
    ii. dialysis;
    iii. hydroxylapatite chromatography;
    iv. gel filtration; and
    v. anion exchange.

17. The method of claim 16, wherein steps (i), (ii), (iii), (iv) and (v) are performed in order.

18. The method of claim 11, wherein the salt content in the medium is greater than about 7.5 g/L.

19. The method of claim 11, wherein the clostripain-producing *Clostridium histolyticum* is ATCC 21000.

* * * * *